United States Patent [19]

Kaetsu et al.

[11] 4,194,066
[45] Mar. 18, 1980

[54] IMMOBILIZATION OF ENZYMES OR BACTERIA CELLS

[75] Inventors: Isao Kaetsu; Minoru Kumkaura, both of Takasaki, Japan

[73] Assignee: Japan Atomic Energy Research Institute, Tokyo, Japan

[21] Appl. No.: 606,209

[22] Filed: Aug. 20, 1975

[30] Foreign Application Priority Data

Aug. 30, 1974 [JP] Japan .................................. 49-99756

[51] Int. Cl.$^2$ .............................................. C07G 7/02
[52] U.S. Cl. .................................................. 435/182
[58] Field of Search .................. 195/63, 68, DIG. 11, 195/59; 424/24

[56] References Cited

U.S. PATENT DOCUMENTS

| | | | |
|---|---|---|---|
| 3,577,512 | 5/1971 | Shepherd et al. | 424/21 |
| 3,859,169 | 1/1975 | O'Driscoll et al. | 195/63 |
| 3,860,490 | 1/1975 | Guttag | 195/59 |
| 3,871,964 | 3/1975 | Huper et al. | 195/63 |
| 3,962,038 | 6/1976 | Kawashima et al. | 195/68 |

*Primary Examiner*—David M. Naff
*Attorney, Agent, or Firm*—Browdy and Neimark

[57] ABSTRACT

A porous polymer containing immobilized enzymes or bacteria cells is prepared by forming a mixture of enzymes or bacteria cells and a monomer having the formulae

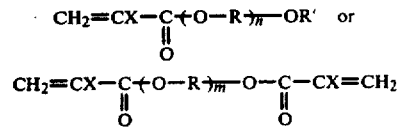

wherein X is hydrogen or methyl; R is $-CH_2CH_2-$,

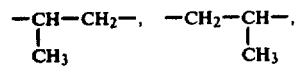

or $-CH_2CH_2CH_2-$, R' is alkyl or hydrogen; n is integer of 2 or more and m is integer of 4 or more, or mixture of such monomers; and then polymerizing or copolymerizing the monomer(s) in the mixture at a temperature of less than 0° C. by means of ionizing radiation.

4 Claims, No Drawings

IMMOBILIZATION OF ENZYMES OR BACTERIA CELLS

BACKGROUND OF THE INVENTION

This invention relates to novel polymer compositions having immobilized bacterial cells and/or immobilized enzyme, in which the enzyme or cells are dispersed within the polymer and to a process for producing the same.

An enzyme industry is one which produces medicine and food by carrying out enzyme reactions in the presence of enzyme or bacterial cells. Recently enzyme industries have become important and have made remarkable progress.

In the prior art, after the enzyme was dissolved in water, the enzyme reaction was effected by using the enzyme or cells solution. In this case, however, after the reaction is completed, the enzyme solution employed in the reaction cannot be reused, because the used enzyme solution contains the resulting reaction product. Therefore, the batch system must be used for the enzyme reaction. In other words, in an enzyme reaction using enzyme solution, maximum effectiveness of the enzyme is not obtained.

In recent years, attempts have been made to prepare an enzyme-polymer composition which could be reused in the enzyme reaction many times. One such composition comprises dispersing the enzyme into a polymeric material or bonding the enzyme to the polymer, and then forming a porous gel or particles from the resulting dispersion. In other words, the research has been directed toward immobilizing an enzyme or making the enzyme insoluble.

For example, one process for immobilizing an enzyme comprises dissolving a water-soluble monomer, such as acrylamide, in an aqueous solution of enzyme, and then simultaneously polymerizing and crosslinking the monomer to form a gel comprising the resulting polymer and the enzyme, and evaporating water from the gel to form a porous material.

Another process for immobilizing an enzyme comprises dissolving a water-soluble polyvinyl alcohol in an enzyme solution and then effecting crosslinking thereof by a known process and evaporating water from the solution to form a porous material. In these processes, the enzyme is dispersed in a water-soluble polymer, whereby the enzyme is immobilized or is made insoluble to some extent.

However, the prior processes have the following disadvantages. In these processes, since the monomer to be polymerized as well as the polymer thus formed are water soluble, the polymer composition obtained by the polymerization is a clear gel in which the enzyme and the polymer are dissolved in water. In order to obtain the porous material necessary for carrying out the enzyme reaction from the gel, the large amount of water contained in the gel must be removed. In addition, the porous material obtained by removing water has large lumps comprising a firm, rigid and porous gel. A satisfactory enzyme reaction cannot be effected by using a lumpy gel, because the total surface area of the large lumps is small. Therefore, in order to carry out the enzyme reaction effectively, the large lumps of gel must be ground or pulverized to increase the surface area of the porous material. However, the removal of water from the gel and grinding the large lumps of gel require much time and much labor. In addition, since the polyacrylamide is noxious, a porous material containing the polyacrylamide and the enzyme is not usable in the food industry.

The present invention eliminates these disadvantages. The present invention provides a porous material obtained by polymerizing a specific monomer containing an enzyme or bacterial cells.

SUMMARY OF THE INVENTION

Therefore, one object of this invention is to provide a process for producing polymer-enzyme or polymer-bacterial cells compositions in which a polymer having different properties from the prior art polymer is used.

Another object of this invention is to provide a process for producing porous material comprising specific polymer and an enzyme or bacterial cells, in which the procedure for immobilizing the enzyme or bacterial cells is simplified and improved.

Another object of the present invention is to provide a porous polymer composition comprising an enzyme or bacterial cells and specific water-insoluble polymer, in which the enzyme or bacterial cells are immobilized or are made insoluble.

Another object of the present invention is to provide a process for producing porous polymer composition comprising an enzyme or bacterial cells and polymer, which is simplified and made more economical.

DETAILED DESCRIPTION OF THE INVENTION

This invention relates to a process for producing porous polymer composition containing immobilized enzyme and/or bacterial cells, characterized by mixing a monomer having the following formula:

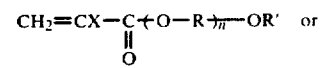

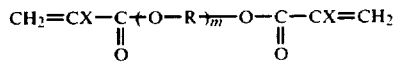

wherein X is hydrogen or methyl; R is —CH$_2$CH$_2$—,

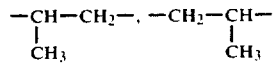

or —CH$_2$CH$_2$CH$_2$—; R' is alkyl, preferably alkyl having carbon atoms of 1–6 or hydrogen; n is integer of two or more and m is integer of 4 or more, or a mixture thereof, with an aqueous solution of enzyme or a dispersion of bacterial cells in water, and then polymerizing and/or copolymerizing the monomers contained in the mixture, thereby depositing the porous polymer material in which the enzyme or cells are dispersed within the polymer.

It is preferred that the polymerization temperature be less than 40° C., most preferably less than 0° C.

This invention further relates to a polymer composition containing immobilized enzyme and/or bacterial cells, characterized in that the enzyme or bacterial cells are dispersed within the polymer, said polymer being prepared by polymerizing and/or copolymerizing a monomer having the following formula:

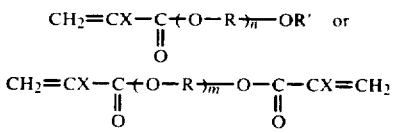

wherein X, R, R', n and m are the same as the above definition.

One enzyme or one kind of bacterial cells may be immobilized according to the present invention. Two or more enzymes or two or more kinds of cells may also be immobilized. Furthermore, a mixture of enzyme and cells may be immobilized.

By "enzyme reaction" we mean a reaction in which an enzyme or cells are employed as a catalyst, an initiator or a reactant.

By the immobilization of enzyme or cells we mean that the enzyme or cells are held by the polymer so that enzyme or cells may be employed in the enzyme reaction many times.

The polymer composition having immobilized enzyme or immobilized cells is a porous, solid material.

The monomers which are employed in this invention are easily miscible with water and are dissolved in the aqueous enzyme solution or in the dispersion of bacterial cells in water over a wide range of concentration. That is, the monomers are dissolved in water or buffer solution which is a dispersing agent for the bacterial cells, thereby uniformly dispersing the cells in the water or buffer solution.

The monomers employed in the present invention have advantages over the acrylamide employed in the prior art in the following points:

(a) The polyacrylamide employed in the prior art is water soluble, whereas the polymers obtained by polymerizing the monomers employed in the present invention are water insoluble and are deposited in the system as the polymerization proceeds.

(b) Upon completion of polymerization, the polymer made from the monomers in the present invention is in the solid state, either in the form of very porous gel or of porous powder. On the other hand, since polyacrylamide is water soluble, it does not pass to a porous solid state only by polymerizing acrylamide monomer.

(c) When the polymer of the present invention is deposited, the polymer closely intertwines with the enzyme or cells to form the deposit of polymer. In addition, since the polymer employed in the present invention tends to crosslink as the polymerization proceeds, the enzyme or cells can be closely held by the polymer.

(d) Polyacrylamide is noxious, whereas the polymer of the present invention is not noxious.

(e) The monomers employed in the present invention are polymerized at a lower dose of an ionizing radiation than polyamide is. Therefore, according to the present invention, the enzyme and cells can be immobilized without their deactivation.

The compounds having the formula:

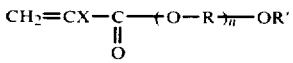

wherein R, X, R' and n are the same as the above definition include methoxydiethylene glycol monomethacrylate, methoxydiethylene glycol monoacrylate, ethoxydiethylene glycol monomethacrylate, ethoxydiethylene glycol monoacrylate, propoxydiethylene glycol monomethacrylate, propoxydiethylene glycol monoacrylate, butoxydiethylene glycol monomethacrylate, butoxydiethylene glycol monoacrylate, pentoxydiethylene glycol monomethacrylate, pentoxydiethylene glycol monoacrylate, hexoxydiethylene glycol monomethacrylate, hexoxydiethylene glycol monoacrylate, methoxytriethylene glycol monomethacrylate, methoxytriethylene glycol monoacrylate, ethoxytriethylene glycol monomethacrylate, ethoxytriethylene glycol monoacrylate, propoxytriethylene glycol monomethacrylate, propoxytriethylene glycol monoacrylate, butoxytriethylene glycol monomethacrylate, butoxytriethylene glycol monoacrylate, methoxytetraethylene glycol monomethacrylate, methoxytetraethylene glycol monoacrylate, ethoxytetraethylene glycol monomethacrylate, ethoxytetraethylene glycol monoacrylate, propoxytetraethylene glycol monomethacrylate, propoxytetraethylene glycol monoacrylate, butoxytetraethylene glycol monomethacrylate, butoxytetraethylene glycol monoacrylate, methoxypentaethylene glycol monomethacrylate, methoxypentaethylene glycol monoacrylate, ethoxypentaethylene glycol monomethacrylate, ethoxypentaethylene glycol monoacrylate, propoxypentaethylene glycol monomethacrylate, propoxypentaethylene glycol monoacrylate, butoxypentaethylene glycol monomethacrylate, butoxypentaethylene glycol monoacrylate, methoxyhexaethylene glycol monomethacrylate, methoxyhexaethylene glycol monoacrylate, ethoxyhexaethylene glycol monomethacrylate, ethoxyhexaethylene glycol monoacrylate, propoxyhexaethylene glycol monomethacrylate, propoxyhexaethylene glycol monoacrylate, butoxyhexaethylene glycol monomethacrylate, butoxyhexaethylene glycol monoacrylate, methoxypolyethylene glycol monomethacrylate, methoxypolyethylene glycol monoacrylate, ethoxypolyethylene glycol monomethacrylate, ethoxypolyethylene glycol monoacrylate, propoxypolyethylene glycol monomethacrylate, propoxypolyethylene glycol monoacrylate, butoxypolyethylene glycol monomethacrylate, butoxypolyethylene glycol monoacrylate, methoxydipropylene glycol monomethacrylate, methoxydipropylene glycol monoacrylate, ethoxydipropylene glycol monomethacrylate, ethoxydipropylene glycol monoacrylate, propoxydipropylene glycol monomethacrylate, propoxydipropylene glycol monoacrylate, butoxydipropylene glycol monomethacrylate, butoxydipropylene glycol monoacrylate, methoxy tripropylene glycol monomethacrylate, methoxytripropylene glycol monoacrylate, ethoxytripropylene glycol monomethacrylate, ethoxytripropylene glycol monoacrylate, propoxytripropylene glycol monomethacrylate, propoxytripropylene glycol monoacrylate, butoxytripropylene glycol monomethacrylate, butoxytripropylene glycol monoacrylate, methoxypolypropylene glycol monomethacrylate, methoxypolypropylene glycol monoacrylate, ethoxypolypropylene glycol monomethacrylate, ethoxypolypropylene glycol monoacrylate, propoxypolypropylene glycol monomethacrylate, propoxypolypropylene glycol monoacrylate, butoxypolypropylene glycol monomethacrylate, butoxypolypropylene glycol monoacrylate, diethylene glycol monomethacrylate, diethylene glycol monoacrylate, triethylene glycol monomethacrylate, triethylene glycol monoacrylate, tetraethylene glycol monomethacrylate, tetraethylene glycol monoacrylate, pentaethylene glycol monomethacrylate, pentaethylene glycol monoacrylate, hexaethylene glycol monomethacrylate, hexaethylene glycol monoacrylate, heptaethylene glycol monomethacrylate, heptaethylene glycol monoacrylate, polyethylene glycol monomethacrylate, polyethylene glycol monoacrylate, dipropylene glycol monomethacrylate, dipropylene glycol monoacrylate, tripropylene glycol monomethacrylate, tripropylene glycol monoacrylate, tetrapropylene glycol monomethacrylate, tetrapropylene glycol monoacrylate, pentapropylene glycol monomethacrylate, pentapropylene glycol monoacrylate, hexapropylene glycol monomethacrylate, hexapropylene glycol monoacrylate, polypropylene glycol monomethacrylate and polypropylene glycol monoacrylate. It is preferred that diethylene glycol monomethacrylate, diethylene glycol monoacrylate, triethylene glycol monomethacrylate, triethylene glycol monoacrylate, tetraethylene glycol monomethacrylate, tetraethylene glycol monoacrylate, polyethylene glycol monomethacrylate, polyethylene glycol monoacrylate, dipropylene glycol monomethacrylate, dipropylene glycol monoacrylate, tripropylene glycol monomethacrylate, tripropylene glycol monoacrylate, polypropylene glycol monomethacrylate, polypropylene glycol monoacrylate, methoxydiethylene glycol monomethacrylate, methoxydiethylene glycol monoacrylate, methoxytriethylene glycol monomethacrylate, methoxytriethylene glycol monoacrylate, methoxytetraethylene glycol monomethacrylate, methoxytetraethylene glycol monoacrylate, methoxypolyethylene glycol monomethacrylate or methoxypolyethylene glycol monoacrylate is used as a monomer which mixes with enzyme or bacterial cells for immobilizing them.

The compounds represented by the formula

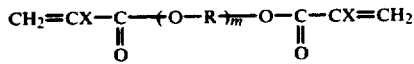

wherein X, R, R' and m are the same as the above definition include diethylene glycol dimethacrylate, diethylene glycol diacrylate, triethylene glycol dimethacrylate, triethylene glycol diacrylate, tetraethylene glycol dimethacrylate, tetraethylene glycol diacrylate, pentaethylene glycol dimethacrylate, pentaethylene glycol diacrylate, hexaethylene glycol dimethacrylate, hexaethylene glycol diacrylate, heptaethylene glycol dimethacrylate, heptaethylene glycol diacrylate, polyethylene glycol dimethacrylate, polyethylene glycol diacrylate, dipropylene glycol dimethacrylate, dipropylene glycol diacrylate, tripropylene glycol dimethacrylate, tripropylene glycol diacrylate, tetrapropylene glycol dimethacrylate, tetrapropylene glycol diacrylate, pentapropylene glycol dimethacrylate, pentapropylene glycol diacrylate, hexapropylene glycol dimethacrylate, hexapropylene glycol diacrylate, heptapropylene glycol dimethacrylate, heptapropylene glycol diacrylate, polypropylene glycol dimethacrylate and polypropylene glycol diacrylate. It is preferred that tetraethylene glycol dimethacrylate, tetraethylene glycol diacrylate, pentaethylene glycol dimethacrylate, pentaethylene glycol diacrylate, hexaethylene glycol dimethacrylate, hexaethylene glycol diacrylate, heptaethylene glycol dimethacrylate, heptaethylene glycol diacrylate, polyethylene glycol dimethacrylate, polyethylene glycol diacrylate, tripropylene glycol dimethacrylate, tripropylene glycol diacrylate, tetrapropylene glycol dimethacrylate, tetrapropylene glycol diacrylate, polypropylene glycol dimethacrylate or polypropylene glycol diacrylate is used as a monomer which mixes with enzyme or bacterial cells for immobilizing them.

Upon completion of the polymerization, the polymer composition containing the enzyme or cells has already become porous. Therefore, this invention does not require the steps of washing, purifying, drying, grinding, etc. The enzyme or cells-polymer composition incorporating the enzyme or cells obtained by polymerizing the monomer in the present invention is usable in the enzyme reaction, as it is.

Even where finely divided powder catalyst is to be used in the enzyme reaction, in many cases, the finely divided powder composed of the enzyme or cells-polymer composition may be prepared only by polymerizing the monomer according to the present invention.

If the finely divided powder cannot be prepared only by polymerizing the monomer, the resulting composition can be easily pulverized by drying it, because the composition is very porous and has large void space. In this case, since water is liberated or removed from the molecules of the enzyme composition, the composition dries quickly, and the composition may be ground after only air drying.

Since the enzyme or cells-polymer composition prepared according to the present invention has large porosity and is easily reduced to a fine powder, diffusion of the reactants in the enzyme reaction is easy. As a result, a high reaction rate can be achieved. In other words, the enzyme or cells-polymer composition prepared according to the present invention is more porous and has more surface area than the enzyme-polymer composition comprising the enzyme and water soluble polymer prepared according to the prior art, so the enzyme reaction activity of the former is greater than that of the latter.

The mixture of the monomer and the enzyme(s) or bacterial cells may be polymerized by a known procedure, such as by adding a catalyst to the polymerizing system, by irradiating the system with ultra sonic vibrations or by irradiating the system with an ionizing radiation. However, since the enzyme tends to be deactivated at an elevated temperature, the polymerization of the monomers in the polymerization system containing the enzyme is preferably effected at as low a temperature as possible in order to prevent the deactivation of the enzyme or cells. Since the polymerization can be effected at a low temperature by means of irradiation, the polymerization method by means of irradiation is preferred. In case of polymerization by using a catalyst, it is preferable to select a catalyst which can initiate the polymerization at a relatively low temperature. The polymerization temperature is preferably less than 40° C., more preferably less than 0° C. Catalysts for satisfying these conditions include ammonium persulfate-sodium thiosulfate, potassium persulfate-sodium thiosulfate, hydrogen peroxide-ferrous salt, potassium persulfate-ferrous salt, potassium persulfate-silver salt, potassium persulfate-hydrazine, and cumene hydroperoxide-polyamine.

Polymerization can also be effected at a low temperature by irradiating the monomer with an ionizing radiation or light. The light wave range includes from visible rays to ultra violet, such as natural rays, high and low pressure mercury lamp. The wave range of the light is selected so that the polymerization may be initiated. The ionizing radiation includes α-rays, β-rays, electron, X-rays, γ-rays, neutron and mixed rays emitted from nuclear reactor. In case of irradiation, the polymerization can be effected at such a low temperature that liquid nitrogen may be present in the polymerization system. The polymerization can also be effected at a low temperature by using an ionizing radiation. Since the monomer employed in the present invention can be polymerized at a low total dose, the enzyme or cell present in the polymerization system is not deactivated. Therefore, the polymerization method by means of irradiation is preferred. The total dose of irradiation is not critical.

This invention also relates to a process for producing porous enzyme or bacterial cells-polymer composition characterized by mixing (a) a monomer having the formula:

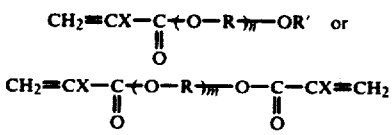

wherein X is hydrogen or methyl; R is $-CH_2CH_2-$,

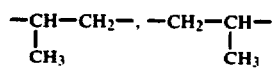

or $-CH_2CH_2CH_2-$; R is hydrogen or alkyl, preferably alkyl having carbon atoms of 1-6, n is integer of two or more and m is integer of 4 or more, or a mixture of such monomers and (b) one or more monomers other than said monomers in the amount of less than 40% by weight, preferably less than 20% by weight on the basis of the total monomer and (c) an aqueous solution of enzyme or a dispersion of cells in water, and then polymerizing the monomers contained in the mixture, thereby depositing the porous polymer composition in which the enzyme or cells are dispersed within the polymer. The polymerization temperature is preferably in the range of less than 40° C., most preferably less than 0° C.

This invention also relates to a porous polymer composition having enzyme and/or cells, characterized in that said polymer is prepared by polymerizing and/or copolymerizing a monomer having the formula

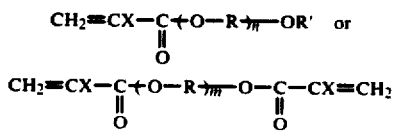

wherein X, R, R', n and m are the same as the above definition or a mixture thereof and one or more monomers other than said monomers in the amount of less than 40% by weight on the basis of the total monomers, and in the composition the enzyme or cells are dispersed within the polymer. It is preferred that the monomers other than the monomers represented by said formulae are employed in the amount of less than 20% by weight on the basis of the total monomer.

The purpose of adding other monomers to the polymerization system is to increase the rate of precipitation of the polymer, to promote separation of water from the system and promote codeposition of the enzyme or cells and the polymer to make the polymer more porous when the polymer deposits, to make the particles of the polymer finer when the polymer deposits, to effectively and simply prepare the enzyme or cells-polymer composition having great activity, to increase the crosslinking property of the polymer, to increase stability of holding or immobilizing the enzyme or bacterial cells in the polymer, and to improve the properties of the resulting enzyme or cells-polymer composition, such as its mechanical strength, its chemical resistance and its thermal stability.

These monomers include ethylene glycol dimethacrylate, ethylene glycol diacrylate, propylene glycol dimethacrylate, propylene glycol diacrylate, butanediol dimethacrylate, butanediol diacrylate, pentanediol dimethaccrylate, pentanediol diacrylate, hexanediol dimethacrylate, hexanediol diacrylate, triethyleneglycol dimethacrylate, triethyleneglycol diacrylate, polyethyleneglycol dimethacrylate, polyethyleneglycol diacrylate, neopentylglycol dimethacrylate, neopentylglycol diacrylate, polypropyleneglycol dimethacrylate, polypropyleneglycol diacrylate, trimethylolpropane trimethacrylate, trimethylolpropane triacrylate, ethyl methacrylate, methyl methacrylate, butyl methacrylate, isobutyl methacrylate, 2-ethylhexyl methacrylate, cyclohexyl methacrylate, furfuryl methacrylate, benzyl methacrylate, glycidyl methacrylate, stearyl methacrylate, octyl methacrylate, ethyl acrylate, methyl acrylate, butyl acrylate, glycidyl acrylate, vinyl acetate, vinyl propionate, butanediol monomethacrylate, butanediol monoacrylate, pentanediol monomethacrylate, pentanediol monoacrylate, hexanediol monomethacrylate, hexanediol monoacrylate, nonanediol monomethacrylate, nonanediol monoacrylate, vinyl stearate, vinyl palmitianate, vinyl pyrrolidone, acrylic acid, methacric acid and a metal salt thereof.

When two or more monomers selected from the group consisting of the monomers having said formulae are used, or when at least one monomer having said formulae and one or more monomers other than said monomers are used, monomers which are more reactive are first polymerized or copolymerized, and then monomers which are less reactive are polymerized. Therefore, in case of using two or more monomers, the polymer composition immobilizing the enzyme and cells may be composed of a mixture of polymer and copolymer.

The present process is applied to a variety of enzymes and bacterial cells to immobilize the enzyme(s) and cells or to make them insoluble thereby keeping the activity of the enzyme and cells. In preparing the polymer composition, the ratio of the enzyme(s) or cells to the monomer is not critical.

The enzymes which are immobilized or are made insoluble by the present invention include urease, alcohol dehydrogenase, lactic dehydrogenase, malic dehydrogenase, glycose oxidase, diamine oxidase, glycose oxidase-catalase, D-amino acid oxidase, liposidase, uricase, ribonuclease, hexokinase, lipase, alkaline phosphatase, acidic phosphatase, nucleoedase, deoxyribonuclease, α-amylase, β-amylase, glucoamylase, glycoseisomerase, cellulase, hemicellulase, β-glucosidase, invertase, anthoxyanase, narindinase, hesperidinase, β-glucuronidase, hyaluronidase, alkaline protease, semialkaline protease, acidic protease, thermorairin, collagenase, pepsinpepsinagen, aminopeptidase, rennin, trypsin-trypsinogen, chymotrypsinogen, elastase, enterodinase, acylase, arginase, L-glutamic acid decarboxylase, L-lysine decarboxylase, and papain.

The bacterial cells which are immobilized or are made insoluble by the present invention include cells containing the above mentioned enzymes, Aerobacteraerogenes, Azotobacter-vinelandi, *Bacillus subtilis*, *Escherrichia* coli and *Micrococcus lysodeikticus*. Other enzymes and bacterial cells can be immobilized or made insoluble according to the present invention.

In carrying out the present invention, polymerizing the monomer(s) and making the resulting polymer porous are simultaneously effected to obtain the powdered enzyme or cells-polymer composition in which the enzyme or cells are dispersed within the polymer. The present invention does not need a purifying step, a drying step (a step for making the gel porous) and a grinding step. According to the present invention, the procedure for immobilizing the enzyme and bacterial cells or making them insoluble is simple in comparison with the prior art, and therefore, the present invention is efficient. Furthermore, the enzyme or cells-polymer composition according to the present invention is obtained in the form of finely divided particles and has large surface area contributing to the enzyme reaction, and has a large void space in the inner part of the composition. Consequently, the method of the present invention is more effective for immobilizing the enzyme than the prior art methods.

The invention is further illustrated, but in no way limited, by the following Examples.

EXAMPLE 1

5 ml of triethylene glycol monomethacrylate was dissolved in 50 ml of a buffer solution, and 25 mg of urease was dissolved in the mixture.

The resulting solution was irradiated with $\gamma$-ray from cobalt 60 having a dose rate of $2 \times 10^5$ R/hr at a total dose of $4 \times 10^5$ R at a temperature of $-30°$ C. to form white polymer precipitate in a yield of 97.6%.

Without effecting purifying and drying steps, the resulting polymer was added to a mixture solution of 20 cc of 0.02 M phosphate buffer solution and 20 cc of 0.02 M urea solution. A conversion of the urea to ammonia and carbon dioxide was effected at a temperature of 25° C. for 30 minutes. From the resulting mixture, 4 cc of sample was withdrawn. To the sample was added 4 cc of 0.1 N HCl to discontinue the reaction. Titration was effected with 0.05 N NaOH to obtain the activity of the enzyme-polymer composition prepared in this Example.

Control test was effected by following the above experiment except that the enzyme was used in the state of solution. Similarly, the activity of the enzyme solution was obtained.

The ratio of the activity of the enzyme-polymer composition of the present invention obtained in Example 1 to the activity of the enzyme solution (hereinunder referred to as the degree of the activity maintained) was 39.6%.

A second experiment was effected by using the same enzyme-polymer composition that was employed in the first experiment. The procedure used in the second experiment was the same as that used in the first experiment. The degree of the activity maintained in the second experiment was 31.1%, Similarly, third and fourth experiments were effected by using the same composition that was employed in the second and third experiments. The results are given in the following.

Table 1

|  | First Experiment | Second experiment | Third experiment | Fourth experiment |
|---|---|---|---|---|
| Degree of activity maintained (%) | 39.6 | 31.1 | 29.9 | 29.9 |

The activity of the enzyme-polymer composition is on the order of about 30% per 100% of the activity of the enzyme solution. However, the enzyme solution is usable for the enzyme reaction only one time, whereas the enzyme-polymer composition of the present invention is usable for the reaction several or more times. Therefore, the enzyme-polymer composition of the present invention is effectively utilized.

EXAMPLE 2

25 mg of $\alpha$-amylase was dissolved in 50 ml of a buffer solution, and 5 ml of polyethylene glycol diacrylate was added and mixed to get a uniform mixture.

The resulting solution was irradiated with $\gamma$-rays from cobalt 60 at a dose rate of $1 \times 10^6$ R/hr for 30 minutes at temperature of 0° C. to form white polymer precipitate in a yield of 95.5%.

Without effecting purifying and drying steps, the resulting polymer was added to 50 ml of a 1% solution of potato starch paste. The starch was converted to maltose at a temperature of 40° C. for 10 minutes. Therefore, 0.1 N HCl was added to the reaction mixture to discontinue the reaction. From the mixture, 5 ml of sample was withdrawn. The sample was added to 100 ml of solution containing 0.005% $I_2$ and 0.05% KI and was shaken. Colorimetric analysis was effected with 10 mm cuvette using wave length of 660 to obtain the activity of the enzymepolymer composition prepared in this Example.

Control test was effected by following the above experiment except that the enzyme was used in the state of solution. Similarly, the activity of the enzyme solution was obtained.

Second, third and fourth experiments were carried out using the same composition that was employed in the first experiment, the same as in Example 1.

The degree of the activity maintained (the ratio of activity of the enzyme-polymer composition prepared by this Example to the activity of the enzyme, namely $\alpha$-amylase solution) was calculated and is shown in Table 2.

Table 2

|  | First experiment | Second experiment | Third experiment | Fourth experiment |
|---|---|---|---|---|
| Degree of activity maintained (%) | 55.2 | 45.6 | 45.5 | 45.5 |

EXAMPLE 3

25 mg of cells containing glucose isomerase was dispersed in 50 ml of a buffer solution, and 2 ml of methoxytriethylene glycol monoacrylate, 2 ml of dipropylene glycol diacrylate and 0.5 ml of vinyl pyrrolidone were added to the dispersion and mixed to get a uniform mixture. The resulting mixture was irradiated with ultraviolet rays at a distance of 10 cm at a temperature of 0° C. for 60 minutes by using a pressure mercury lamp made by Toshiba to obtain white polymer.

Without effecting purifying and drying steps, the resulting polymer was added to 20 ml of a glucose solution dissolved in a phosphate buffer solution containing $Mg^{++}$. The glucose was converted to fructose at temperature of 70° C. for an hour. 4 ml of sample was withdrawn from the resulting solution, and the sample was rendered colored through cystein-carbasole reaction. The amount of fructose thus formed was determined from color comparison of 560 m$\mu$, whereby the activity of the enzyme-polymer composition prepared according to this Example was calculated.

Control test was effected by following the above experiment except that the enzyme was used in the state of solution. Similarly, the activity of the enzyme solution was obtained.

The experiment was repeated 30 times, using the same composition that was employed in the first experiment the same may as in Example 1. The degree of catalyst activity maintained in the 30th experiment was more than 30%.

EXAMPLE 4

5 mg of cells containing glucose isomerase was dispersed in 50 ml of a buffer solution, and 4 ml of tetraethylene glycol diacrylate, 0.2 ml of trimethylol propane trimethacrylate and 0.5 ml of acrylamide were added to the dispersion and mixed to get a uniform mixture. To the resulting mixture was added 0.5% solution of ammonium persulfate-ferrous sulfate. This mixture was heated at a temperature of 40° C. for 10 hours to deposit white polymer.

Without effecting purifying and drying steps, the resulting polymer was added to 20 ml of a glucose solution dissolved in a phosphate buffer solution containing $Mg^{++}$. The glucose was converted to fructose at a temperature of 70° C. for an hour. 4 ml of sample was withdrawn from the resulting solution, and the sample was rendered colored through cystein-carbasole reaction. The amount of fructose thus formed was determined from color comparison of 560 m$\mu$ whereby the activity of the enzyme-polymer composition prepared according to this Example was calculated.

Control test was effected by following the above experiment except that the enzyme was used in the state of solution. Similarly the activity of the enzyme solution was obtained.

The experiment was repeated 30 times, using the same composition that was employed in the first experiment the same way as in Example 1. The degree of catalyst activity maintained in the 30th experiment was more than 25%.

EXAMPLE 5

25 mg of glucose isomerase was dissolved in 50 ml of a buffer solution, and 10 ml of methoxypolyethylene glycol monoacrylate was added to the solution and mixed to get a uniform mixture. The resulting mixture was cooled to a temperature of −80° C. by using dry ice-methanol, and was irradiated with γ-ray from cobalt 60 at a dose rate of $1 \times 10^6$ R/hr. After irradiation, the mixture was gradually heated to an ambient temperature, whereby polymerization of the monoacrylate is caused over 60 minutes to obtain white, porous polymer.

Without effecting purifying and drying steps, the resulting polymer was added to a glass column. A buffer solution containing glucose was contacted with the enzyme-polymer composition at a temperature of 70° C. by passing the solution through the column to convert glucose to fructose. The amount of fructose thus formed was determined by Takasaki's Method to obtain the activity of the enzyme-polymer composition prepared in this Example.

Control test was effected by following the above experiment except that the enzyme was used in the state of solution. Similarly, the activity of the enzyme solution was obtained. The above enzyme-polymer composition was continuously employed through 20 days as a catalyst for enzyme-reaction. After the above employment, the degree of the activity of the enzyme-polymer composition maintained was as high as 90%.

EXAMPLE 6

Example 5 was repeated except that the mixture containing methoxypolyethylene glycol monoacrylate and glucose isomerase was irradiated with an electron accelerator of 2.5 MeV at a total dose of $1 \times 10^6$ R. After the continuous employment for 20 days, the degree of the activity of the enzyme-polymer composition maintained was a high as 84%.

What is claimed is:

1. A process for producing a porous polymer composition containing immobilized enzymes and/or immobilized bacterial cells which comprises:

forming a mixture consisting essentially of an enzyme solution or a dispersion of bacterial cells and a monomer having the formula

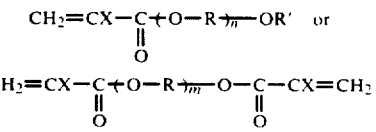

wherein X is hydrogen or methyl, R is $-CH_2CH_2-$,

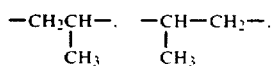

or $-CH_2CH_2CH_2-$, R' is hydrogen or alkyl, n is an integer of 2 or more and m is an integer of 4 or more, or a mixture of such monomers; and then polymerizing and/or copolymerizing the monomer(s) containied in the mixture at a temperature of less than 0° C. by means of an ionizing radiation, thereby depositing the polymer containing enzyme and/or cells from water.

2. A process for producing a porous polymer composition containing immobilized enzyme and/or immobilized bacterial cells which comprises:

mixing (a) an enzyme solution or a dispersion of bacterial cells, (b) a monomer having the formula

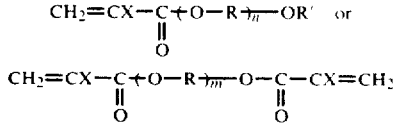

wherein X is hydrogen or methyl, R is —CH$_2$CH$_2$—,

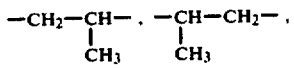

or —CH$_2$CH$_2$CH$_2$—, R' is hydrogen or alkyl, n is an integer of 2 or more and m is an integer of 4 or more, or a mixture of such monomers, and (c) one or more monomers other than said (b) monomers in the amount of less than 40% by weight on the basis of the total monomers; and then polymerizing and/or copolymerizing the monomers contained in the mixture, at a temperature of less than 0° C. by means of an ionizing radiation, thereby depositing the polymer containing enzyme and/or cells from water.

3. The porous polymer composition prepared by the process of claim 1, containing immobilized enzyme and/or immobilized bacterial cells, characterized in that in said composition the enzyme or cells are dispersed within the polymer.

4. The porous polymer composition prepared by the process of claim 2, containing immobilized enzyme and/or immobilized bacterial cells, characterized in that in said compositions the enzyme or cells are dispersed within the polymer.

* * * * *